United States Patent [19]
Failli et al.

[11] Patent Number: 5,563,145
[45] Date of Patent: Oct. 8, 1996

[54] RAPAMYCIN 42-OXIMES AND HYDROXYLAMINES

[75] Inventors: Amedeo A. Failli, Princeton Junction, N.J.; Guy A. Schiehser, Yardley; Oleg I. Bleyman, Holland, both of Pa.

[73] Assignee: American Home Products Corporation, Madison, N.J.

[21] Appl. No.: 350,557

[22] Filed: Dec. 7, 1994

[51] Int. Cl.⁶ .................. A61K 31/445; C07D 491/16
[52] U.S. Cl. .................. 514/291; 540/456; 546/14; 514/183
[58] Field of Search .................. 540/456; 514/183, 514/291

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit | 424/122 |
| 4,375,464 | 3/1983 | Sehgal et al. | 424/122 |
| 4,401,653 | 8/1983 | Eng | 424/114 |
| 4,650,803 | 3/1987 | Stella et al. | 514/291 |
| 4,885,171 | 12/1989 | Surendra et al. | 424/122 |
| 5,023,262 | 6/1991 | Caufield et al. | 514/291 |
| 5,023,263 | 6/1991 | Von Burg | 514/291 |
| 5,023,264 | 6/1991 | Caufield et al. | 514/291 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,883 | 3/1992 | Schiehser | 514/183 |
| 5,100,899 | 3/1992 | Calne | 514/291 |
| 5,102,876 | 4/1992 | Caufield | 514/183 |
| 5,118,677 | 6/1992 | Caufield | 514/183 |
| 5,118,678 | 6/1992 | Kao et al. | 514/183 |
| 5,120,842 | 6/1992 | Faillie et al. | 540/452 |
| 5,130,307 | 7/1992 | Failli et al. | 514/321 |
| 5,138,051 | 8/1992 | Hughes et al. | 540/456 |
| 5,151,413 | 9/1992 | Caufield et al. | 514/63 |
| 5,169,851 | 12/1992 | Hughes et al. | 514/291 |
| 5,177,203 | 1/1993 | Failli et al. | 540/456 |
| 5,194,447 | 3/1993 | Kao | 514/542 |
| 5,221,670 | 7/1993 | Caufield | 514/183 |
| 5,233,036 | 8/1993 | Hughes | 540/455 |
| 5,260,300 | 11/1993 | Hu | 514/291 |
| 5,302,584 | 4/1994 | Kao et al. | 514/80 |
| 5,373,014 | 12/1994 | Failli et al. | 514/291 |
| 5,378,836 | 1/1995 | Kao et al. | 540/456 |
| 5,385,908 | 1/1995 | Nelson et al. | 514/291 |
| 5,385,909 | 1/1995 | Nelson et al. | 514/291 |
| 5,385,910 | 1/1995 | Ocain et al. | 514/291 |

FOREIGN PATENT DOCUMENTS

| | | | |
|---|---|---|---|
| 507555A1 | 7/1992 | European Pat. Off. | 540/456 |
| WO9405300 | 3/1994 | WIPO | 540/456 |

OTHER PUBLICATIONS

Vezina, C., J. Antibiot. 28:721 (1975).
Sehgal, S. N., J. Antibot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11 (pt. 2):197 (1992).
Stepkowski, S. M., Transplantation Proc. 23:507 (1991).

*Primary Examiner*—Alan L. Rotman
*Attorney, Agent, or Firm*—Arnold S. Milowsky

[57] ABSTRACT

A compound of the structure

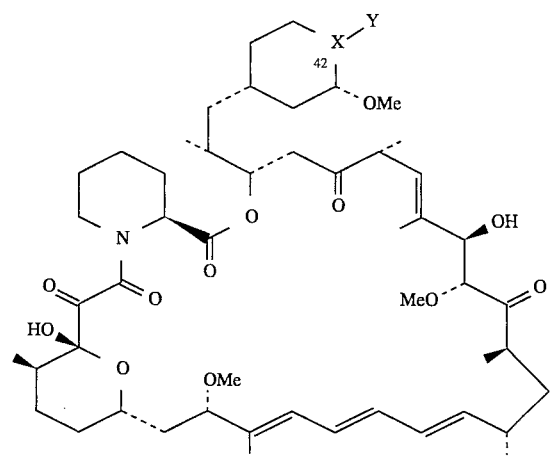

wherein X-Y is C=NOR¹ or CHNHOR²;

R¹ and R² are each, independently, hydrogen, alkyl, alkenyl, alkynyl, aminoalkyl, alkylaminoalkyl, dialkylaminoalkyl, cycloalkyl, alkyloxy, alkoxyalkyl, cycloalkylaminoalkyl, cyanoalkyl, fluoroalkyl, trifluoromethylalkyl, trifluoromethyl, ArO—, —(CH$_2$)$_m$Ar, or —COR³;

R³ is alkyl of 1–6 carbon atoms, —NH$_2$, —NHR⁴, —NR⁴R⁵, or –OR⁴;

R⁴ and R⁵ are each, independently, alkyl, Ar or if both are present can be taken together to form a 4–7 membered ring;

Ar is an aryl or heteroaryl radical which may be optionally substituted; and m=0–6; or a pharmaceutically acceptable salt thereof, which is useful as an immunosuppressive, antiinflammatory, antifungal, antiproliferative, and antitumor agent.

15 Claims, No Drawings

RAPAMYCIN 42-OXIMES AND HYDROXYLAMINES

BACKGROUND OF THE INVENTION

This invention relates to rapamycin 42-oximes and hydroxylamines and a method for using them for inducing immunosuppression, and in the treatment of transplantation rejection, graft vs. host disease, autoimmune diseases, diseases of inflammation, adult T-cell leukemia/lymphoma, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31,539 (1978); U.S. Pat. No. 3,929,992; and U.S. Pat. No. 3,993,749].

Rapamycin alone (U.S. Pat. No. 4,885,171 ) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)l, smooth muscle cell proliferation and intimal thickening following vascular injury [Morris, R. J. Heart Lung Transplant 11 (pt. 2): 197 (1992)], adult T-cell leukemia/lymphoma [European Patent Application 525,960 A1], and ocular inflammation [European Patent Application 532,862 A1 ].

Mono- and diacylated derivatives of rapamycin (esterified at the 28 and 43 positions) have been shown to be useful as antifungal agents (U.S. Pat. No. 4,316,885) and used to make water soluble aminoacyl prodrugs of rapamycin (U.S. Pat. No. 4,650,803). Recently, the numbering convention for rapamycin has been changed; therefore according to Chemical Abstracts nomenclature, the esters described above would be at the 31- and 42- positions. U.S. Pat. No. 5,023,263 describes the preparation and use of 42-oxorapamycin and U.S. Pat. No. 5,023,264 describes the preparation and use of 27-oximes of rapamycin.

DESCRIPTION OF THE INVENTION

This invention provides derivatives of rapamycin which are useful as immunosuppressive, antiinflammatory, antifungal, antiproliferative, and antitumor agents having the structure

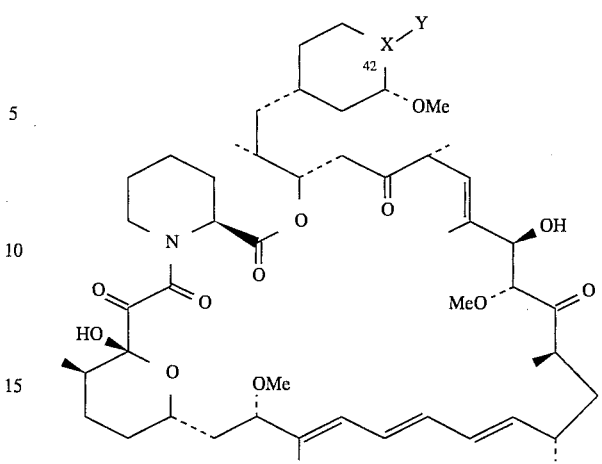

wherein X-Y is C=NOR$^1$ or CHNHOR$^2$;

R$^1$ and R$^2$ are each, independently, hydrogen, alkyl of 1–6 carbon atoms, alkenyl of 2–7 carbon atoms, alkynyl of 2–7 carbon atoms, aminoalkyl of 1–6 carbon atoms, alkylaminoalkyl of 1–6 carbon atoms per alkyl group, dialkylaminoalkyl of 1–6 carbon atoms per alkyl group, cycloalkyl of 3–8 carbon atoms, alkyloxy of 1–6 carbon atoms, alkoxyalkyl of 1–6 carbon atoms per alkyl group, cycloalkylaminoalkyl of 4–14 carbon atoms, cyanoalkyl of 2–77 carbon atoms, fluoroalkyl of 1–6 carbon atoms, trifluoromethylalkyl of 2–77 carbon atoms, trifluoromethyl, ArO—, —(CH$_2$)$_m$Ar, or —COR$_3$;

R$^3$ is alkyl of 1–6 carbon atoms, —NH$_2$, —NHR$^4$, —NR$^4$R$^5$, or —OR$_4$;

R$^4$ and R$^5$ are each, independently, alkyl of 1–6 carbon atoms, Ar or if both are present can be taken together to form a 4–7 membered ring;

Ar is an aryl or heteroaryl radical which may be optionally mono-, di-, or tri-substituted with a group selected from alkyl of 1–6 carbon atoms, alkenyl of 2–77 carbon atoms, alkynyl of 2–77 carbon atoms, arylalkyl of 7–10 carbon atoms, alkoxy of 1–6 carbon atoms, cyano, halo, hydroxy, nitro, carbalkoxy of 2–77 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–712 carbon atoms, alkylthio of 1–6 carbon atoms, —SO$_3$H, and —CO$_2$H; and m=0–6;

or a pharmaceutically acceptable salt thereof.

The pharmaceutically acceptable salts are those derived from such inorganic cations such as sodium, potassium, and the like; organic bases such as: mono-, di-, and trialkyl amines of 1–6 carbon atoms, per alkyl group and mono-, di-, and trihydroxyalkyl amines of 1–6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The terms alkyl of 1–6 carbon atoms, alkenyl of 2–77 carbon atoms, and alkynyl of 2–77 carbon atoms, include both straight chain as well as branched carbon chains. By virtue of possessing a double bond, the oximes of this invention possess cis-trans isomerism and hence this invention embraces not only geometrical isomer mixtures, but also the individual E and Z isomers, which can be separated by methods known to those skilled in the art. Likewise, the hydroxylamines of this invention consist of mixtures of epimers at C-42, and hence this invention embraces not only the isomer mixture, but also the individual isomers, which can be separated by methods known to those skilled in the art.

It is preferred that the aryl and heteroaryl radicals of Ar are phenyl, pyridyl, fury, pyrrolyl, thiophenyl, imidazolyl, oxazolyl, or thiazolyl that may be optionally mono-, di-, or tri-substituted with a group selected from alkyl of 1–6 carbon atoms, alkenyl of 2–77 carbon atoms, alkynyl of 2–77 carbon atoms, arylalkyl of 7–10 carbon atoms, alkoxy of 1–6 carbon atoms, cyano, halo, hydroxy, nitro, carbalkoxy of 2–77 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, $-SO_3H$, and $-CO_2H$.

When $R^3$ is $-NR^4R^5$, the $R^4$ and $R^5$ groups can be the same or different (as defined above) or can be taken together to form a saturated heterocycle having 4–7 atoms in the ring of which 1 atom is a nitrogen and 0–2 other ring atoms can be nitrogen, oxygen, or sulfur. In the case where $R^4$ and $R^5$ are taken together, it is preferred that $R4R^5$ is a carbon chain forming an azetidine, pyrrolidine, piperidine, or homopiperidine ring.

Of the compounds of this invention preferred members are those in which X-Y is $C=NOR^1$; those in which X-Y is $C=NOR^1$ and $R^1$ is hydrogen, alkyl of 1–6 carbon atoms, alkenyl of 2–77 carbon atoms, alkynyl of 2–77 carbon atoms, alkyloxy of 1–6 carbon atoms, $-(CH_2)_mAr$, or $-COR_3$; those in which X-Y is $CHNHOR_2$; those in which $CHNHOR^2$, and $R^2$ is hydrogen or $-(CH_2)_mAr$.

The compounds of this invention can be prepared from 42-oxorapamycin, which can be prepared in moderate yield by selectively oxidizing the 42-position of rapamycin via a ruthenium mediated oxidation as taught in U.S. Pat. No. 5,023,263, which is hereby incorporated by reference. Alternatively, 42-oxorapamycin can be prepared in approximately 50% yield using tetrapropylammonium perruthenate/ N-methylmorpholine N-oxide, as taught by Holt in PCT Publication U.S. 93/0668. 42-oxorapamycin can then be treated with an appropriately substituted hydroxylamine to provide mixture of 42-(E) and (Z) oximes (X-Y is $C=NOR^1$), which can be separated by standard methodology. The 42-oximes can further reacted with a suitable reducing agent, such as sodiron cyanoborohydride/THF/ dioxane/pH 3.5, to provide the hydroxylamines of this invention (X-Y is $CHNHOR^2$).

Compounds of this invention in which X-Y is $C=NOR^1$ and $R^1$ is a carbonyl containing moiety can be prepared from rapamycin 42-oxime (X-Y is $C=NOR^1$ and $R^1$ is hydrogen). For example, rapamycin 42-oxime can be reacted with sodium cyanate to produce the compound in which $R^1$ is $-COR^3$ and $R^3$ is $NH_2$. Similarly, rapamycin 42-oxime can be treated with a suitable substituted isocyanate or haloacylamine [i.e., $R^4R^5NC(O)Cl$] to provide compounds in which $R^1$ is—$COR^3$ and $R^3$ is—$NR^4R^5$. Compounds in which $R^1$ is $-COR^3$ and $R^3$ is $-NHR^4$ can be prepared analogously. Additionally, treatment of rapamycin 42-oxime with an appropriate alkyl- or arylchloroformate in pyridine and a solvent such as methylene chloride provides oxime carbonates in which $R^1$ is $-COR^3$, and $R^3$ is alkyl or Ar.

Analogous functionalization can be obtained when X-Y is $CHNHOR^2$, starting from the compound in which $R^2$ is hydrogen (obtained by the cyanoborohydride reduction of rapamycin 42-oxime).

As an alternative to the ruthenium based oxidative preparation of 42-oxorapamycin, this invention also provides a synthetic route to the oximes and hydroxylamines of this invention via the Dess-Martin periodinane oxidation of a 31-O-protected rapamycin. The protection of the 31-position of rapamycin has been described in U.S. Pat. No. 5,120,842, which is hereby incorporated by reference. For example, the treatment of rapamycin with a suitable protecting reagent such as triethylsilyl triflate/2,6-utidine/methylene chloride, followed by acetic acid/THF/water provides 31-O-triethylsilyl rapamycin in quantitative yield. Oxidation with Dess-Martin periodinane provides 31-O-triethylsilyl-42-oxorapamycin in about 65% yield, which can then be treated with a suitable hydroxylamine (and subsequently derivatized) as described above. For the oximes of this invention, the triethylsilyl protecting group can be removed under mildly acidic conditions (acetic acid/THF/water) as described in U.S. Pat. No. 5,120,842. Using this route, the hydroxylamines of this invention can also be produced from the corresponding oximes via cyanoborohydride reduction under acidic conditions, with concomitant removal of the silyl protecting group.

Based on the above described Dess-Martin periodinane methodology, the following compounds are intermediates useful in the preparation of the oximes of this invention.

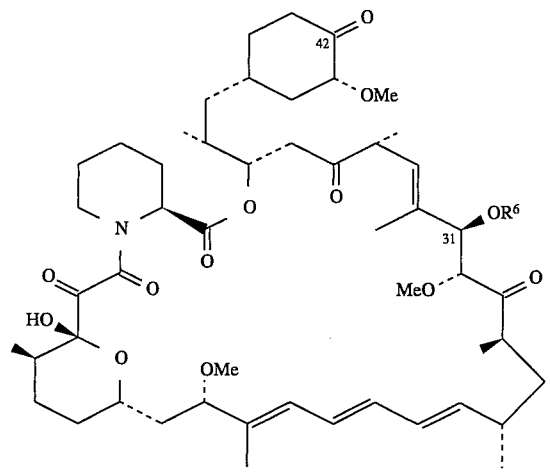

wherein $R^6$ is $-SiR^7R^8R^9$; and $R^7$, $R^8$, and $R^9$ are each, independently, alkyl of 1–8 carbon atoms, alkenyl of 1–8 carbon atoms, phenylalkyl of 7–10 carbon atoms, triphenylmethyl, or phenyl.

Of the above intermediates, the compound of Example 1 is the preferred intermediate.

The reagents used in the preparation of the compounds of this invention can be either commercially obtained or can be prepared by standard procedures described in the literature.

Immunosuppressive activity for representative compounds of this invention was evaluated in an in vitro standard pharmacological test procedure to measure the inhibition of lymphocyte proliferation (LAF) and in two in vivo standard pharmacological test procedures. The pinch skin graft test procedure measures the immunosuppressive activity of the compound tested as well as the ability of the compound tested to inhibit or treat transplant rejection. The adjuvant arthritis standard pharmacological test procedure measures the ability of the compound tested to inhibit immune mediated inflammation. The adjuvant arthritis test procedure is a standard pharmacological test procedure for rheumatoid arthritis. The procedures for these standard pharmacological test procedures are provided below.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An $IC_{50}$ was obtained for each test compound as well as for rapamycin. When evaluated as a comparator for the representative compounds of this invention, rapamycin had an $IC_{50}$ ranging from 0.5 to 3.3 nM. The results obtained are provided as an $IC_{50}$ and as the percent inhibition of T-cell proliferation at 0.1 µM. The results obtained for the representative compounds of this invention were also expressed as a ratio compared with rapamycin. A positive ratio indicates immunosuppressive activity. A ratio of greater than 1 indicates that the test compound inhibited thymocyte proliferation to a greater extent than rapamycin. Calculation of the ratio is shown below.

$$\frac{IC_{50} \text{ of Rapamycin}}{IC_{50} \text{ of Test Compound}}$$

Representative compounds of this invention were also evaluated in an in vivo test procedure designed to determine the survival time of pinch skin graft from male BALB/c donors transplanted to male C₃H(H-2K) recipients. The method is adapted from Billingham R. E. and Medawar P. B., J. Exp. Biol. 28:385–402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days ±S.D.) of the drug treatment group was compared with the control group. Results are expressed as the mean survival time in days. Untreated (control) pinch skin grafts are usually rejected within 6–7 days. Compounds were tested using a dose of 4 mg/kg, i.p. A survival time of 11.67±0.63 days was obtained for rapamycin at 4 mg/kg, i.p.

The adjuvant arthritis standard pharmacological test procedure measures the ability of test compounds to prevent immune mediated inflammation and inhibit or treat rheumatoid arthritis. The following briefly describes the test procedure used. A group of rats (male inbread Wistar Lewis rats) are pre-treated with the compound to be tested (1 h prior to antigen) and then injected with Freud's Complete Adjuvant (FCA) in the right hind paw to induce arthritis. The rats are then orally dosed on a Monday, Wednesday, Friday schedule from day 0–14 for a total of 7 doses. Both hind paws are measured on days 16, 23, and 30. The difference in paw volume (mL) from day 16 to day 0 is determined and a percent change from control is obtained. The left hind paw (uninjected paw) inflammation is caused by T-cell mediated inflammation and is recorded as % change from control. The right hind paw inflammation, on the other hand, is caused by nonspecific inflammation. Compounds were tested at a dose of 2 mg/kg. The results are expressed as the percent change in the uninjected paw at day 16 versus control; the more negative the percent change, the more potent the compound. Rapamycin provided −70% change versus control, indicating that rapamycin treated rats had 70% less immune induced inflammation than control rats.

The results obtained in these standard pharmacological test procedures are provided following the procedure for making the specific compounds that were tested.

The results of these standard pharmacological test procedures demonstrate immunosuppressive activity both in vitro and in vivo for the compounds of this invention. The results obtained in the LAF test procedure indicates suppression of T-cell proliferation, thereby demonstrating the immunosuppressive activity of the compounds of this invention. Further demonstration of the utility of the compounds of this invention as immunosuppressive agents was shown by the results obtained in the skin graft and adjuvant arthritis standard pharmacological test procedures. Additionally, the results obtained in the skin graft test procedure further demonstrates the ability of the compounds of this invention to treat or inhibit transplantation rejection. The results obtained in the adjuvant arthritis standard pharmacological test procedure further demonstrate the ability of the compounds of this invention to treat or inhibit rheumatoid arthritis.

Based on the results of these standard pharmacological test procedures, the compounds are useful in the treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like), and eye uveitis.

Because of the activity profile obtained, the compounds of this invention also are considered to have antitumor, antifungal activities, and antiproliferative activities. The compounds of this invention therefore also useful in treating solid tumors, adult T-cell leukemia/lymphoma, fungal infections, and hyperproliferative vascular diseases such as restenosis and atherosclerosis. When used for restenosis, it is preferred that the compounds of this invention are used to treat restenosis that occurs following an angioplasty procedure. When used for this purpose, the compounds of this invention can be administered prior to the procedure, during the procedure, subsequent to the procedure, or any combination of the above.

When administered for the treatment or inhibition of the above disease states, the compounds of this invention can be administered to a mammal orally, parenterally, intranasally, intrabronchially, transdermally, topically, intravaginally, or rectally.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The compounds of this invention can be formulated neat or with a pharmaceutical carder to a mammal in need thereof. The pharmaceutical carder may be solid or liquid. When formulated orally, it has been found that 0.01% Tween 80 in PHOSAL PG-50 (phospholipid concentrate with 1,2-propylene glycol, A. Nattermann & Cie. GmbH) provides an acceptable oral formulation.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carder is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carder can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which am sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 μg/kg–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation and biological activities of representative compounds of this invention.

EXAMPLE 1

31-O-(Triethylsilyl)-42-oxorapamycin

Step A. 31-O-(Triethylsilyl)rapamycin

To a solution of rapamycin (15.39 g, 16.84 mmole) and 2,6-utidine (7.65 g, 75.76 ml) in dichloromethane (100 ml) at 0° C., triethylsilyl trifluoromethane sulfonate (10 g, 37.88 mmole) was added dropwise over 30 minutes. The mixture was stirred at 0° C. for another 90 minutes, and filtered. The tiltrate was diluted with ethyl acetate (500 ml), washed with water (3×250 ml) and brine (1×100 ml), dried (MgSO$_4$) and evaporated to dryness. The material was redissolved in anhydrous THF (40 ml), cooled to 0° C. and treated with ice-cold glacial acetic acid (150 ml) and water (80 ml). The mixture was stirred for 3 hours at 0° C., diluted with ethyl acetate (500 ml) and carefully brought to pH 7–8 with NaHCO$_3$ at 0° C. The organic layer was washed with water (2×250 ml), brine (1×100 ml), dried (MgSO$_4$) and evaporated to dryness to provide the title product in quantitative yield.

$^1$H NMR (CDCl$_3$, 400 MHz): δ 1.66 (3H, 6-CH$_3$C=C), 1.75 (3H, 30-CH$_3$C=C), 3.14 (3H, 41-OCH$_3$), 3.27 (3H, 7-CH$_3$O), 3.40 (3H, 32-CH$_3$O), 4.12 (m, 1H, 31-CH)

MS (neg. ion FAB, m/z): 1027.4 [M]$^-$, 589.3.

Step B. 31-O-(Triethylsilyl)-42-oxorapamycin

A mixture of 31-O-(triethylsilyl)rapamycin (17.32 g, 16.84 mmole) and Dess-Martin periodinane (8.65 g, 20.35 mmole) in anhydrous dichloromethane (150 ml) was stirred under nitrogen for 5 hours. The mixture was filtered, the tiltrate diluted with ethyl acetate (500 ml) and washed with water (3×250 ml) and brine (1×100 ml), dried (MgSO$_4$) and evaporated to dryness. The crude material was preabsorbed on a silica Merck-60 column and flashed with hexane-ethyl acetate 95:5 and 7:2, to provide pure title product in 64.9% yield.

$^1$H NMR (CDCl$_3$, 400 MHz): δ 0.42–0.48 (m, 9H), 0.80–0.83 (m, 6H), 1.61 (3H, 6 -CH$_3$C=C), 1.77 (3H, 30-CH$_3$C=C), 3.04 (3H, 41-OCH$_3$), 3.16 (3H, 7-OCH$_3$), 3.28 (3H, 32-CH$_3$O), 3.90 (m, 1H, 41-CH).

MS (neg. ion FAB, m/z): 1025.3 [M]$^-$.

EXAMPLE 2

42-Deoxo-42-(hydroxyimino)rapamycin

Preparation A

A mixture of 42-oxorapamycin (0.183 g, 0.22 mmole; prepared via the method described in U.S. Pat. No. 5,023, 263), hydroxylamine hydrochloride (0.0143 g, 0.22 mmole) and sodium acetate (0.025 g, 0.3 mmole) in methanol (5 ml), was stirred under nitrogen for 15 minutes. The mixture was evaporated to dryness and the residue was purified by flash chromatography (on Merck-60 silica gel, eluant 50% THF in hexane). The pure fractions were combined, evaporated and the resulting oil was recrystallized from isopropyl ether/ cyclohexane 20:80 to provide the title product as a mixture of E/Z isomers (0.075 g, 40% yield).

$^1$H NMR (CDCl$_3$, 400 MHz): δ 1.65 (3H, 6-CH$_3$C=C)), 1.75 (3H, 30-CH$_3$C=C), 3.13 (3H, 41-OCH$_3$), 3.34 (3H, 7-OCH$_3$), 3.41 (3H, 32-OCH$_3$) $^{13}$C NMR (CDCl$_3$, 400 MHz): δ 215.28, 208.17, 169.26, 166.72, 158.83, 140.60, 140.07, 135.95, 135.67, 133.56, 130.18, 129.47, 126.62, 126.43, 98.48, 86.33, 84,73, 84.30, 78.90, 67.17, 59.29, 59.13, 57.51, 55.93, 55.88, 51.234, 46.58, 46.04, 44.19, 41.47, 40.65, 40.19, 38.93, 38.41, 37.71, 35.08, 33.78, 33.24, 32.05, 32.00, 31.82, 31.21, 30.92, 27.21, 27.05, 26.89, 25.27, 22.84, 21.97, 21.62, 21.46, 20.64, 16.32, 16.22, 16.09, 15.99, 14.74, 13.60, 13.18, 13.10, 10.33, 10.15

MS (neg. ion FAB, m/z): 926 [M]$^-$, 590, 334

Anal. Calcd. for C$_{51}$H$_{78}$N$_2$O$_{13}$: C, 66.07; H, 8.48; N, 3.02; Found: C, 66.25; H, 8.67; N, 3.03.

Preparation B

Step A. 31-O-(Triethylsilyl)-42-deoxo-42-(hydroxyimino)rapamycin

Under anhydrous conditions, a mixture of 31-O-(triethylsilyl)-42-oxorapamycin of Example 1 (0.105 g, 0.102 mmole), hydroxylamine hydrochloride (7.6 mg, 0.109 mmole), and sodium acetate (12.5 mg, 0.153 mmol ) in anhydrous methanol (5 ml) was stirred for 30 minutes. The mixture was filtered and the tiltrate evaporated to dryness. The residue was redissolved in ethyl acetate (50 ml), washed with water (2×50 ml) and brine (1×50 ml), dried (MgSO$_4$), and evaporated to dryness to provide the title product as a mixture of E/Z isomers (0.114 g, 94% yield).

$^1$H NMR (CDCl$_3$, 400MHz): δ 0.47–0.55 (m, 9H), 0.84–0.88 (m, 6H), 1.65 (3H, 6-CH$_3$C=C), 1.75 (3H, 30-CH$_3$C=C), 3.14 (3H, 41-OCH$_3$), 3.26 (3H, 7-OCH$_3$), 3.44 (3H, 32-OCH$_3$)

MS (neg. ion FAB, m/z): 1040.7 [M]$^-$.

Step B. 42-Deoxo-42-(hydroxyimino)rapamycin

A solution of 31-O-(triethylsilyl)-42-deoxo-42-(hydroxyimino)rapamycin (1 g, 0.974 mmole) in 20 ml of a 10% solution of p-toluenesulfonic acid in methanol, was stirred for one hour under nitrogen at 0° C. The solution was diluted with ethyl acetate and quenched with 5% aqueous NaHCO$_3$. The organic layer was washed with water and brine, dried (MgSO4) and evaporated to dryness to provide the title product, identical with the material described in Preparation A (0.812 g, 89.9% yield).

Results obtained in standard pharmacological test procedures:

LAF IC$_{50}$: 3.88 nM

LAF ratio: 0.85

Skin graft survival: 10.8±0.4

EXAMPLE 3

42-Deoxo-42-(hydroxyamino)rapamycin

To a solution of 31-O-(triethylsilyl)-42-deoxo-42-(hydroxyimino)rapamycin of Example 2, Preparation B, Step A (2.08 g, 2 mmol) in anhydrous methanol (75 ml) under nitrogen and at 0° C., were simultaneously added over a 30 minute period, a 1N-solution of sodium cyanoborohydride in tetrahydrofuran (2 ml ) and a 4N HCl solution in dioxane, so as to maintain the pH at 3.5. The mixture was stirred for 30 minutes,, diluted with EtOAc and washed with 2.5% NaHCO$_3$ (100 ml), water (2×250 ml) and brine (1×250 ml), dried (MgSO$_4$), and evaporated to dryness to provide the title compound as a mixture of isomers (0.763 g, 41% yield).

$^1$H NMR (CDCl$_{13}$, 400MHz): δ 1.60 and 1.63 (3H, 6-CH$_3$C=C), 1.72 and 1.74 (3H, 30-CH$_3$C=C), 3.09 and 3.11 (3H, 41-OCH3), 3.28, 3.32, 3.34 and 3.36 (6H, 7- and 32-OCH$_3$)

MS (neg. ion FAB, m/z): 928.4 [M]$^-$, 590.3, 336.6

Anal.: Calcd. for C$_{51}$H$_{80}$N$_2$O$_{13}$: C, 65.92; H, 8.68; N, 3.01; Found: C, 65.36; H, 8.53; N, 2.82.

Results obtained in standard pharmacological test procedures:

LAF IC$_{50}$: 5.60 nM

LAF ratio: 0.18

Skin graft survival: 9.6±0.0

Percent change in adjuvant arthritis versus control: −84%

EXAMPLE 4

42-Deoxy-42-oxorapamycin-42-O-carbamoyloxime

A mixture of 42-deoxo-42-(oxyimino)rapamycin of Example 2 (0.813 g, 0.876 mmole), sodium cyanate (0.228 g, 3.5 ), glacial acetic acid (8 ml) and water (8 ml) was stirred for 1.5 hours under nitrogen. The mixture was diluted with ethyl acetate (100 ml) and quenched with aqueous NaHCO$_3$. The organic layer was washed with water and brine, dried (MgSO$_4$), and evaporated to dryness. The crude product was dissolved in dichloromethane, preabsorbed on silica gel Merck-60 and purified by flash chromatography (step gradient from 50% ethyl acetate in hexane to pure ethyl acetate) to provide the title product as a mixture of E/Z isomers (0.289 g, 34% yield).

$^1$H NMR (CDCl$_3$, 400 MHz): δ 1.66 (3H, 6-CH$_3$C=C), 1.75 (3H, 30-CH$_3$C=C).

3.14 (3H, 41-OCH$_3$), 3.33 (3H, 7-OCH$_3$), 3.43 (3H, 32-OCH$_3$) $^{13}$C NMR (CDC$_{13}$, 400MHz): d 215.17, 208.11, 169.67, 169.30, 166.73, 164.31, 164.25, 156.37, 156.33, 140.05, 138.34, 137.28, 136.07, 135.78, 135.09, 133.51, 133.25, 132.17, 130.61, 130.22, 130.05, 129.40, 127.33, 126.81, 126.66, 126.57, 126.44, 125.76, 125.50, 125.22, 98.70, 98.50, 84.73, 84.34, 84.28, 82.70, 78.92, 68.91, 67.21, 59.29, 57.93, 57.82, 56.34, 56.31, 56.16, 56.09, 55.85, 55.56, 52.00, 51.25, 46.55, 46.06, 45.68, 44.54, 44.18, 41.92, 41.83, 41.48, 41.40, 41.26, 41.14, 41.01, 40.88, 40.57, 40.42, 40.35, 40.19, 39.77, 39.30, 39.17, 38.97, 38.83, 38.66, 38.59, 37.98, 37.45, 37.26, 35.53, 35.13, 34.88, 34.79, 34.72, 34.57, 33.83, 33.49, 33.37, 33.31, 33.24, 32.19, 32.03, 31.98, 31.85, 21.70, 31.64, 31.20, 27.35, 27.21, 27.03, 26.80, 25.23, 25.04, 24.45, 24.31, 21.62, 21.51, 21.37, 20.99, 20.74, 20.63, 16.69, 16.30, 16.18, 15.95, 15.80, 15.71, 15.03, 14.57, 13.88, 13.64, 13.18, 13.13, 13.07, 10.16

MS (neg. ion FAB, m/z): 969.8 $[M]^-$, 925.8 $[M-CONH_2]^-$, 590.6.

Results obtained in standard pharmacological test procedures:

LAF $IC_{50}$: 2.00 nM

LAF ratio: 0.25

Skin graft survival: 9.5±1.1

EXAMPLE 5

42-Deoxy-42-oxorapamycin 42-[O-(pyridin-2-ylmethyl)]-oxime

The title compound was prepared according to Examples 2, Preparation B, except for replacing hydroxylamine hydrochloride with 0-(pyridine-2-ylmethyl) hydroxylamine dihydrochloride (71.1% yield).

$^1$H NMR (CDCl$_3$, 400MHz): δ 1.654 (3H, 6-CH$_3$C=C), 1.75 1 (3H, 30-CH$_3$C=C).

3.138 (3H, 41-OCH$_3$), 3.334 (3H, 7-OCH$_3$), 3.338 (3H, 32-OCH$_3$), 7.17–8.58 (mm, 4H, Harom).

$^{13}$C NMR (CDCl$_3$, 400MHz): δ 158.96 (42-C=NO—)

MS (neg. ion FAB, m/z): 1017.5 $[M]^-$, 590.4, 425.3.

Results obtained in standard pharmacological test procedures:

LAF $IC_{50}$: 1.50 nM

LAF ratio: 0.40

Skin graft survival: 7.8±0.8

Percent change in adjuvant arthritis versus control: −53%

EXAMPLE 6

42-Deoxy-42-oxorapamycin 42-[O-(pyridin-4-ylmethyl)]-oxime

The title compound was prepared according to Example 2, Preparation B, except for replacing hydroxylamine hydrochloride with 0-(pyridine-4-ylmethyl)-hydroxylamine dihydrochloride (34.5% yield).

$^1$H NMR (CDCl$_3$, 400MHz): δ 1.653 (3H, 6-CH$_3$C=C), 1.753 (3H, 30-CH$_3$C=C).

3.153 (3H, 41-OCH$_3$), 3.29 (2×3H, 7-OCH$_3$ and 32-OCH$_3$), 7.2 (m, 2H, Harom), 8.52 (m, 2H, Harom).

MS (neg. ion FAB, m/z): 1017.2 $[M]^-$, 590.2, 425.1.

Results obtained in standard pharmacological test procedures:

LAF $IC_{50}$: 1.80 nM

LAF ratio: 0.31

Skin graft survival: 8.0±0.9

EXAMPLE 7

2-Deoxy-42-oxoxapamycin 42-[O-(tert-butyl)]-oxime

The title compound was prepared according to Examples 2, Preparation B, except for replacing hydroxylamine hydrochloride with O-(tert-butyl)-hydroxylamine hydrochloride (25.6% yield).

$^1$H NMR (CDCl$_3$, 400MHz): δ 1.28 (9H, tert-butyl), 1.654 (3H, 6-CH$_3$C=C), 1,75 (3H, 30-CH$_3$C=C), 3.136 (3H, 41-OCH$_3$), 3.336 (3H, 7-OCH$_3$), 3.37 (3H, 32-OCH$_3$)

$^3$C NMR (CDCl$_3$, 400MHz): δ 155.89 (42-C=NO—)

MS (neg. ion FAB, m/z): 982.5 $[M]^-$, 590.3, 390.2.

Results obtained in standard pharmacological test procedures:

LAF: 49% inhibition at 0.1 μM

EXAMPLE 8

42-Deoxy-42-oxorapamycin 42-[O-(phenylmethyl)]-oxime

The title compound was prepared according to Examples 2, Preparation B, except for replacing hydroxylamine hydrochloride with O-(phenylmethyl)-hydroxylamine hydrochloride (29.9% yield).

$^1$H NMR (CDCl$_3$, 400 MHz): δ 5 1.652 (3H, 6-CH$_3$C=C), 1.747 (3H, 30-CH$_3$C=C).

3.136 (3H, 41-OCH$_3$), 3.332 (3H, 7-OCH$_3$), 3.35 (3H, 32-OCH$_3$), 5.134 (2H, =NOCH$_2$—, at C-42), 7.27–7.37 (m, 5H, Harom)

$^{13}$C NMR (CDCl$_3$, 400 MHz): δ 158.48 (42-C=NO-)

MS (neg. ion FAB, m/z): 1016.2 $[M]^-$, 590.2, 424.1.

Results obtained in standard pharmacological test procedures:

LAF IC50: 21.67 nM

LAF ratio: 0.03

EXAMPLE 9

42-Deoxy-42-oxorapamycin 42-(O-allyl)-oxime

The title compound was prepared according to Example 2, Preparation B, except for replacing hydroxylamine hydrochloride with O-(allyl)-hydroxylamine hydrochloride (57.1% yield).

$^1$H NMR (CDCl$_3$, 400 MHz): a 1.655 (3H, 6-CH$_3$C=C), 1.751 (3H, 30-CH$_3$C=C).

3.139 (3H, 41-OCH$_3$), 3.336 (3H, 7-OCH$_3$), 3.395 (3H, 32-OCH$_3$), 4.60 (m, 2H,

=NOCH$_2$C=, at C-42), 5.17–5.31 (m, 2H, —C=CH$_2$, at C-42), 5.94–6.03 (m, 1H,

—CCH=C—, at C-42).

$^{13}$C NMR (CDCl$_3$, 400 MHz): δ 158.1 (42-C=N-O-)

MS (neg. ion FAB, m/z): 966.5 $[M]^-$, 590.3, 374.2.

Results obtained in standard pharmacological test procedures:

LAF 43% inhibition at 0.1 μM

EXAMPLE 10

42-Deoxy-42-oxorapamycin 42-[O-(prop-2-ynyl)]-oxime

The title compound was prepared according to Example 2, Preparation B, except for replacing hydroxylamine hydrochloride with O-(prop-2-ynyl)-hydroxylamine hydrochloride (35.4% yield).

$^1$H NMR (CDCl$_3$, 400 MHz): δ 1.66 (3H, 6-CH$_3$C=C), 1.75 (3H, 30-CH$_3$C=C).

3.13 (3H, 41-OCH$_3$), 3.33 (3H, 7-OCH$_3$), 3.415 (3H, 32-OCH$_3$), 4.69 (2H, =NOCH$_2$C at C-42)

$^{13}$C NMR (CDCl$_3$, 400 MHz): δ 159.5 (42-C=NO-)

MS (neg. ion FAB, m/z): 964.2 [M]$^-$, 590.2, 372.1.

Results obtained in standard pharmacological test procedures:

LAF IC50: 8.13 nM

LAF ratio: 0.08

Skin graft survival: 8.0±1.1.

EXAMPLE 11

42-Deoxo-42-[O-(pyridin-4-ylmethyl)]-hydroxyamino rapamycin

The title compound was prepared according to Example 3, except for replacing 31-O-(triethylsilyl)-42-deoxo-42-hydroxyimino rapamycin with 42-deoxy-42-oxo rapamycin 42-[O-(pyridin-4-ylmethyl)]-oxime of Example 6.

MS (neg. ion FAB, m/z): 1019.5 [M]$^-$.

What is claimed is:

1. A compound of the structure

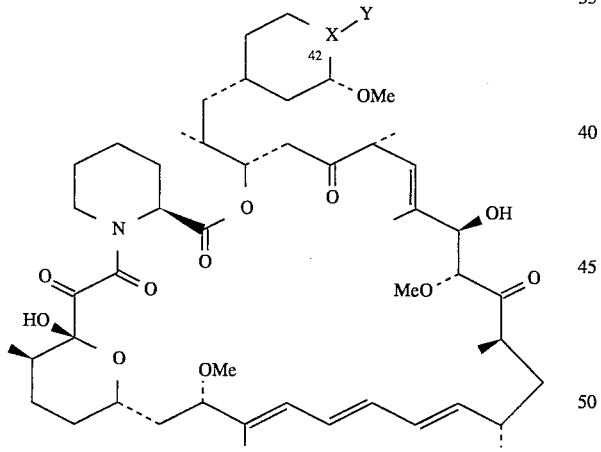

wherein X-Y is C=NOR$^1$;

R$^1$ is hydrogen, alkyl of 1–6 carbon atoms, alkenyl of 2–7 carbon atoms, alkynyl of 2–7 carbon atoms, aminoalkyl of 1–6 carbon atoms, alkylaminoalkyl of 1–6 carbon atoms per alkyl group, dialkylaminoalkyl of 1–6 carbon atoms per alkyl group, cycloalkyl of 3–8 carbon atoms, alkyloxy of 1–6 carbon atoms, alkoxyalkyl of 1–6 carbon atoms per alkyl group, cycloalkylaminoalkyl of 4–14 carbon atoms, cyanoalkyl of 2–7 carbon atoms, fluoroalkyl of 1–6 carbon atoms, trifluoromethylalkyl of 2–7 carbon atoms, trifluoromethyl, ArO—, or —(CH$_2$)$_m$Ar Ar is phenyl, pyridyl, fury, pyrrolyl, thiophenyl, imidazolyl, oxazolyl, or thiazolyl which may be optionally mono-, di-, or tri-substituted with a group selected from alkyl of 1–6 carbon atoms, alkenyl of 2–7 carbon atoms, alkynyl of 2–7 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, and —CO$_2$H; and m=0–6;

or a pharmaceutically acceptable salt thereof.

2. The compound of claim 1, wherein R$^1$ is hydrogen, alkyl of 1–6 carbon atoms, alkenyl of 2–7 carbon atoms, alkynyl of 2–7 carbon atoms, alkyloxy of 1–6 carbon atoms, or —(CH$_2$)$_m$Ar or a pharmaceutically acceptable salt thereof.

3. The compound of claim 1 which is 42-deoxo-42-(hydroxyimino)rapamycin or a pharmaceutically acceptable salt thereof.

4. The compound of claim 1 which is 42-deoxy-42-oxorapamycin 42-[O -(pyridin-2-ylmethyl)]-oxime or a pharmaceutically acceptable salt thereof.

5. The compound of claim 1 which is 42-deoxy-42-oxorapamycin 42-[O -(pyridin-4-ylmethyl)]-oxime or a pharmaceutically acceptable salt thereof.

6. The compound of claim 1 which is 42-deoxy-42-oxorapamycin 42-[O-(tert-butyl)]-oxime or a pharmaceutically acceptable salt thereof.

7. The compound of claim 1 which is 42-deoxy-42-oxorapamycin 42-[O-(phenylmethyl)]-oxime or a pharmaceutically acceptable salt thereof.

8. The compound of claim 1 which is 42-deoxy-42-oxorapamycin 42-(O-allyl)-oxime or a pharmaceutically acceptable salt thereof.

9. The compound of claim 1 which is 42-deoxy-42-oxorapamycin 42-[O-(prop-2 -ynyl)]-oxime or a pharmaceutically acceptable salt thereof.

10. A method of treating transplantation rejection or graft vs. host disease in a mammal in need thereof, which comprises administering to said mammal an antirejection effective amount of a compound of the structure

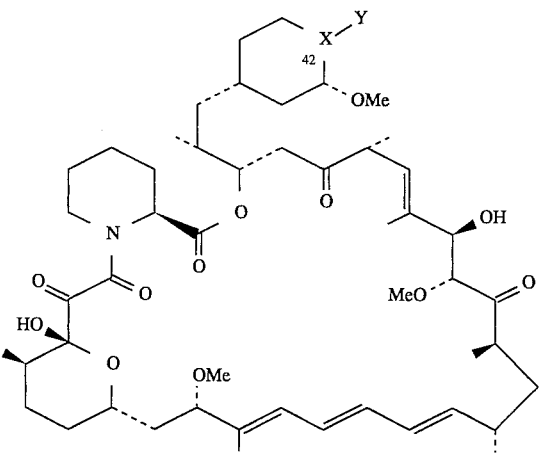

wherein X-Y is C=NOR$^1$;

R$^1$ is hydrogen, alkyl of 1–6 carbon atoms, alkenyl of 2–7 carbon atoms, alkynyl of 2–7 carbon atoms, aminoalkyl of 1–6 carbon atoms, alkylaminoalkyl of 1–6 carbon atoms per alkyl group, dialkylaminoalkyl of 1–6 carbon atoms per alkyl group, cycloalkyl of 3–8 carbon atoms, alkyloxy of 1–6 carbon atoms, alkoxyalkyl of 1–6 carbon atoms per alkyl group, cycloalkylaminoalkyl of 4–14 carbon atoms, cyanoalkyl of 2–7 carbon atoms, fluoroalkyl of 1–6 carbon atoms, trifluoromethylalkyl of 2–7 carbon atoms, trifluoromethyl, ArO—, or —(CH$_2$)$_m$Ar Ar is phenyl, pyridyl, fury, pyrrolyl, thiophenyl, imidazolyl, oxazolyl, or thiazolyl which may be optionally mono-, di-, or tri-substituted with a group selected from alkyl of 1–6 carbon atoms, alkenyl of 2–7 carbon atoms, alkynyl of 2–7 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, and —CO$_2$H; and m=0–6;

or a pharmaceutically acceptable salt thereof.

11. A method of treating a fungal infection in a mammal in need thereof, which comprises administering to said mammal an antifungal effective amount of a compound of the structure

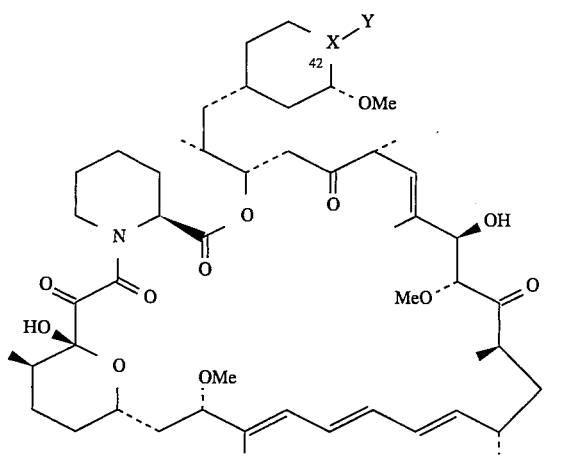

wherein X-Y is C=NOR$^1$;

R$^1$ is hydrogen, alkyl of 1–6 carbon atoms, alkenyl of 2–7 carbon atoms, alkynyl of 2–7 carbon atoms, aminoalkyl of 1–6 carbon atoms, alkylaminoalkyl of 1–6 carbon atoms per alkyl group, dialkylaminoalkyl of 1–6 carbon atoms per alkyl group, cycloalkyl of 3–8 carbon atoms, alkyloxy of 1–6 carbon atoms, alkoxyalkyl of 1–6 carbon atoms per alkyl group, cycloalkylaminoalkyl of 4–14 carbon atoms, cyanoalkyl of 2–7 carbon atoms, fluoroalkyl of 1–6 carbon atoms, trifluoromethylalkyl of 2–7 carbon atoms, trifluoromethyl, ArO—, or —(CH$_2$)$_m$Ar Ar is phenyl, pyridyl, fury, pyrrolyl, thiophenyl, imidazolyl, oxazolyl, or thiazolyl which may be optionally mono-, di-, or tri-substituted with a group selected from alkyl of 1–6 carbon atoms, alkenyl of 2–7 carbon atoms, alkynyl of 2–7 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, and —CO$_2$H; and m=0–6;

or a pharmaceutically acceptable salt thereof.

12. A method of treating rheumatoid arthritis in a mammal in need thereof, which comprises administering to said mammal an antiarthritis effective amount of a compound of the structure

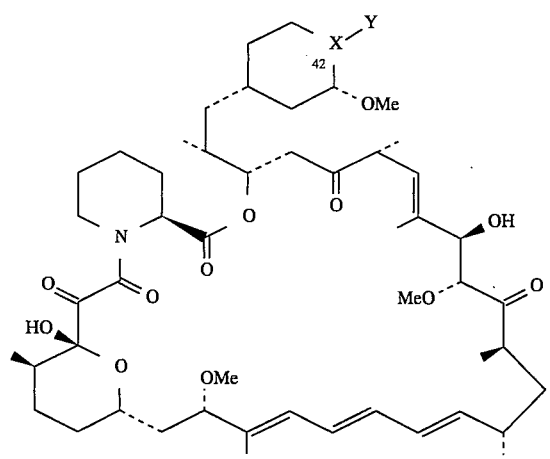

wherein X-Y is C=NOR$^1$;

R$^1$ is hydrogen, alkyl of 1–6 carbon atoms, alkenyl of 2–7 carbon atoms, alkynyl of 2–7 carbon atoms, aminoalkyl of 1–6 carbon atoms, alkylaminoalkyl of 1–6 carbon atoms per alkyl group, dialkylaminoalkyl of 1–6 carbon atoms per alkyl group, cycloalkyl of 3–8 carbon atoms, alkyloxy of 1–6 carbon atoms, alkoxyalkyl of 1–6 carbon atoms per alkyl group, cycloalkylaminoalkyl of 4–14 carbon atoms, cyanoalkyl of 2–7 carbon atoms, fluoroalkyl of 1–6 carbon atoms, trifluoromethylalkyl of 2–7 carbon atoms, trifluoromethyl, ArO—, or —(CH$_2$)$_m$Ar Ar is phenyl, pyridyl, fury, pyrrolyl, thiophenyl, imidazolyl, oxazolyl, or thiazolyl which may be optionally mono-, di-, or tri-substituted with a group selected from alkyl of 1–6 carbon atoms, alkenyl of 2–7 carbon atoms, alkynyl of 2–7 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, and —CO$_2$H; and m=0–6;

or a pharmaceutically acceptable salt thereof.

13. A method of treating restenosis in a mammal in need thereof, which comprises administering to said mammal an antiproliferative effective amount of a compound of the structure

17

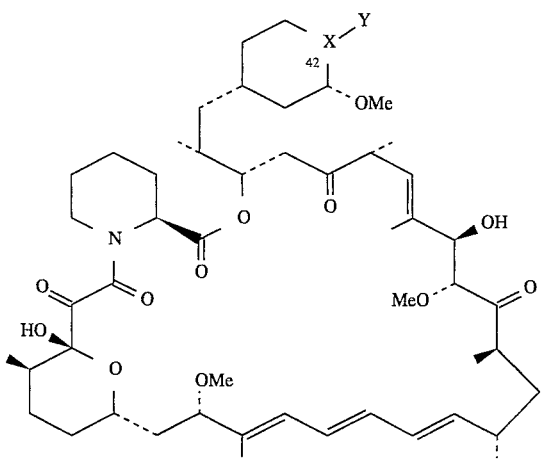

wherein X-Y is C=NOR¹;

R¹ is hydrogen, alkyl of 1–6 carbon atoms, alkenyl of 2–7 carbon atoms, alkynyl of 2–7 carbon atoms, aminoalkyl of 1–6 carbon atoms, alkylaminoalkyl of 1–6 carbon atoms per alkyl group, dialkylaminoalkyl of 1–6 carbon atoms per alkyl group, cycloalkyl of 3–8 carbon atoms, alkyloxy of 1–6 carbon atoms, alkoxyalkyl of 1–6 carbon atoms per alkyl group, cycloalkylaminoalkyl of 4–14 carbon atoms, cyanoalkyl of 2–7 carbon atoms, fluoroalkyl of 1–6 carbon atoms, trifluoromethylalkyl of 2–7 carbon atoms, trifluoromethyl, ArO—, or —(CH$_2$)$_m$Ar Ar is phenyl, pyridyl, fury, pyrrolyl, thiophenyl, imidazolyl, oxazolyl, or thiazolyl which may be optionally mono-, di-, or tri-substituted with a group selected from alkyl of 1–6 carbon atoms, alkenyl of 2–7 carbon atoms, alkynyl of 2–7 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO,H, and —CO$_2$H; and m=0–6;

or a pharmaceutically acceptable salt thereof.

14. A method of treating pulmonary inflammation in a mammal in need thereof, which comprises administering to said mammal an antiinflammatory effective amount of a compound of the structure

18

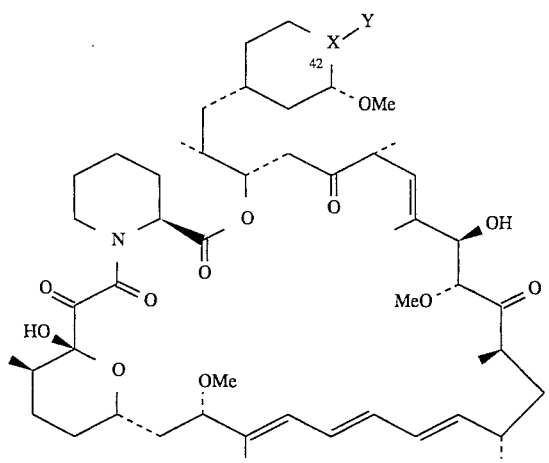

wherein X-Y is C=NOR¹;

R¹ is hydrogen, alkyl of 1–6 carbon atoms, alkenyl of 2–7 carbon atoms, alkynyl of 2–7 carbon atoms, aminoalkyl of 1–6 carbon atoms, alkylaminoalkyl of 1–6 carbon atoms per alkyl group, dialkylaminoalkyl of 1–6 carbon atoms per alkyl group, cycloalkyl of 3–8 carbon atoms, alkyloxy of 1–6 carbon atoms, alkoxyalkyl of 1–6 carbon atoms per alkyl group, cycloalkylaminoalkyl of 4–14 carbon atoms, cyanoalkyl of 2–7 carbon atoms, fluoroalkyl of 1–6 carbon atoms, trifluoromethylalkyl of 2–7 carbon atoms, trifluoromethyl, ArO—, or —(CH$_2$)$_m$Ar Ar is phenyl, pyridyl, fury, pyrrolyl, thiophenyl, imidazolyl, oxazolyl, or thiazolyl which may be optionally mono-, di-, or tri-substituted with a group selected from alkyl of 1–6 carbon atoms, alkenyl of 2–7 carbon atoms, alkynyl of 2–7 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, and —CO$_2$H; and m=0–6;

or a pharmaceutically acceptable salt thereof.

15. A pharmaceutical composition which comprises a compound of the structure

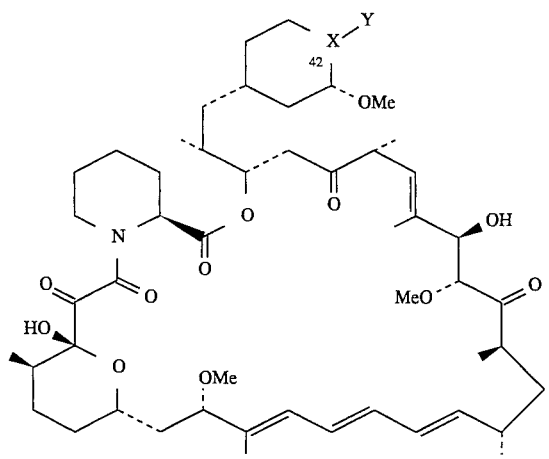

wherein X-Y is C=NOR$^1$;

R$^1$ is hydrogen, alkyl of 1–6 carbon atoms, alkenyl of 2–7 carbon atoms, alkynyl of 2–7 carbon atoms, aminoalkyl of 1–6 carbon atoms, alkylaminoalkyl of 1–6 carbon atoms per alkyl group, dialkylaminoalkyl of 1–6 carbon atoms per alkyl group, cycloalkyl of 3–8 carbon atoms, alkyloxy of 1–6 carbon atoms, alkoxyalkyl of 1–6 carbon atoms per alkyl group, cycloalkylaminoalkyl of 4–14 carbon atoms, cyanoalkyl of 2–7 carbon atoms, fluoroalkyl of 1–6 carbon atoms, trifluoromethylalkyl of 2–7 carbon atoms, trifluoromethyl, ArO—, or —(CH$_2$)$_m$Ar Ar is phenyl, pyridyl, fury, pyrrolyl, thiophenyl, imidazolyl, oxazolyl, or thiazolyl which may be optionally mono-, di-, or tri-substituted with a group selected from alkyl of 1–6 carbon atoms, alkenyl of 2–7 carbon atoms, alkynyl of 2–7 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, and —CO$_2$H; and m=0–6;

or a pharmaceutically acceptable salt thereof, and a pharmaceutical carrier.

* * * * *